US010058039B2

(12) United States Patent
D'Aoust et al.

(10) Patent No.: US 10,058,039 B2
(45) Date of Patent: Aug. 28, 2018

(54) PLANT INFILTRATION DEVICE

(71) Applicant: MEDICAGO INC., Quebec (CA)

(72) Inventors: Marc-Andre D'Aoust, Quebec (CA); Nicole Bechtold, Quebec (CA); Luc Laurin, Brossard (CA); Louis-Philippe Vezina, Neuville (CA); Normand Dubuc, St-Lambert (CA)

(73) Assignee: MEDICAGO INC., Québec (CA)

( * ) Notice: Subject to any disclaimer, the term of this patent is extended or adjusted under 35 U.S.C. 154(b) by 602 days.

(21) Appl. No.: 14/379,202

(22) PCT Filed: Feb. 15, 2013

(86) PCT No.: PCT/CA2013/050118
§ 371 (c)(1),
(2) Date: Aug. 15, 2014

(87) PCT Pub. No.: WO2013/120204
PCT Pub. Date: Aug. 22, 2013

(65) Prior Publication Data
US 2015/0351326 A1    Dec. 10, 2015

Related U.S. Application Data

(60) Provisional application No. 61/599,094, filed on Feb. 15, 2012.

(51) Int. Cl.
*A01M 21/04* (2006.01)
*A01M 7/00* (2006.01)
(Continued)

(52) U.S. Cl.
CPC ............... *A01G 7/06* (2013.01); *A01G 7/00* (2013.01); *A01G 22/00* (2018.02); *C12N 15/8205* (2013.01)

(58) Field of Classification Search
USPC ............... 47/1.5, 1.7, 57.7, DIG. 11, 58.1 R
See application file for complete search history.

(56) References Cited

U.S. PATENT DOCUMENTS 577,021 A * 2/1897 Groszmann ............... E03D 1/20
4/365
2,745,217 A * 5/1956 Gold ........................ A01G 7/00
134/121
(Continued)

FOREIGN PATENT DOCUMENTS

| EP | 2085481 | 8/2009 |
| WO | WO 00/42835 | 7/2000 |
| WO | WO 2009/095183 | 8/2009 |

OTHER PUBLICATIONS

International Search Report and Written Opinion in International Application No. PCT/CA2013/050118 dated May 14, 2013.
(Continued)

*Primary Examiner* — Andrea Valenti
(74) *Attorney, Agent, or Firm* — Norton Rose Fulbright US LLP

(57) ABSTRACT

It is provided a plant infiltration device for infiltrating plants with an inoculum and method of using same, the device comprising a frame having one or more tray racks adapted for receiving at least one tray of plants to be infiltrated; an automated manipulation mechanism mounted to the frame and operable to displace the plant trays within the device; a plurality of inoculum reservoirs mounted to the frame and containing one or more inoculum fluids; an infiltration tank mounted to the frame and within which the plant trays are received when disposed in the infiltration position; and a vacuum generating device in communication with the infiltration tank to apply a negative pressure within the infiltration tank, thereby opening pores of the plant leaves
(Continued)

Figure 1:
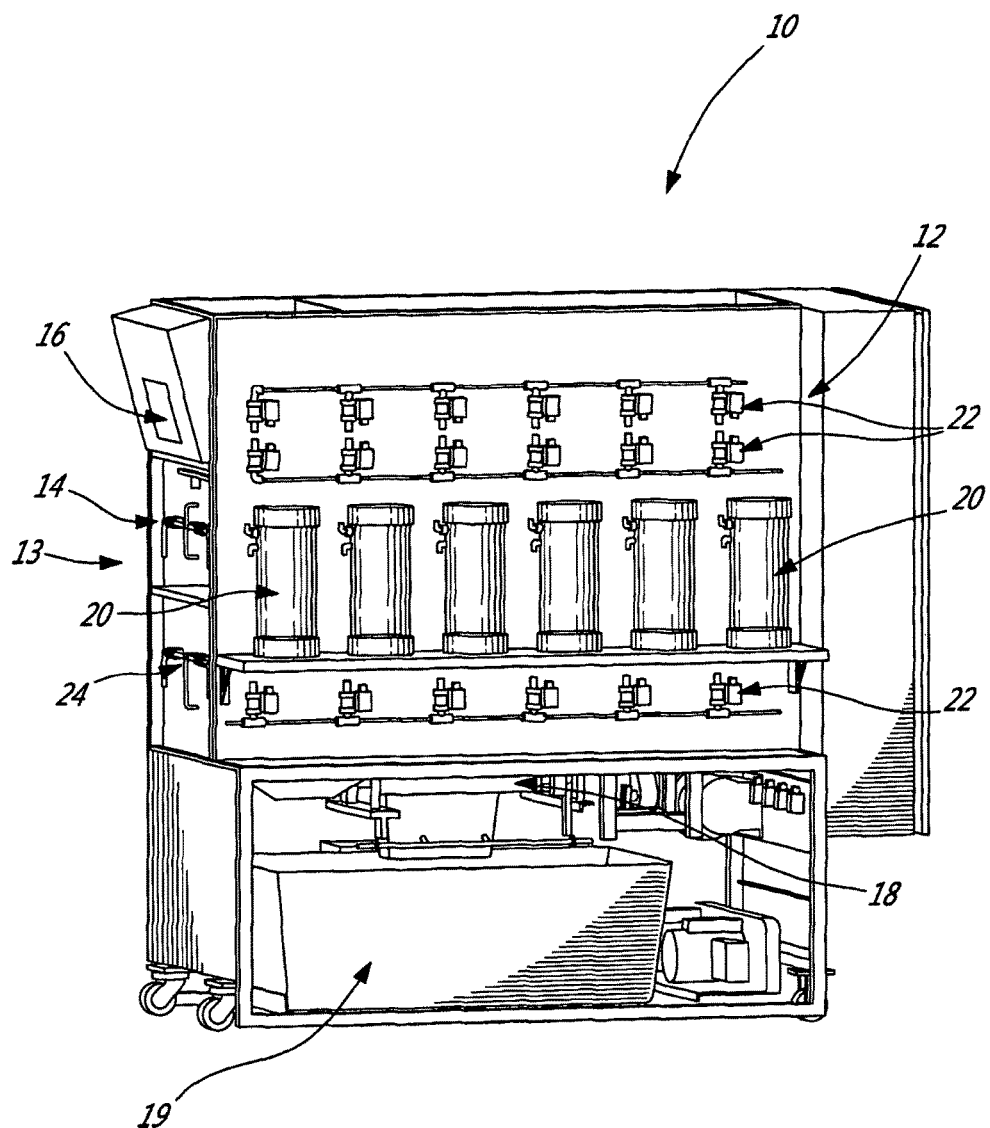

immersed in the inoculum within the infiltration tank and causing the inoculum fluid to infiltrate into the plant leaves.

27 Claims, 14 Drawing Sheets

(51) Int. Cl.
| | |
|---|---|
| *A01G 7/06* | (2006.01) |
| *A01G 22/00* | (2018.01) |
| *A01G 7/00* | (2006.01) |
| *C12N 15/82* | (2006.01) |

(56) References Cited

U.S. PATENT DOCUMENTS

| | | | | |
|---|---|---|---|---|
| 3,683,547 A | * | 8/1972 | Harden | A01G 25/09 118/323 |
| 4,882,875 A | * | 11/1989 | Green | A01G 27/02 47/48.5 |
| 6,695,143 B2 | * | 2/2004 | Alm | B65D 11/10 206/464 |
| 7,905,054 B1 | | 3/2011 | Metzler | 47/57.5 |
| 9,512,439 B2 | * | 12/2016 | Carraro | C12N 15/8205 |
| 2005/0155101 A1 | | 7/2005 | Akai et al. | 800/278 |
| 2010/0299785 A1 | * | 11/2010 | Dujardin | C12N 15/8205 800/278 |
| 2014/0290135 A1 | * | 10/2014 | Carraro | C12N 15/8205 47/57.7 |
| 2015/0181812 A1 | * | 7/2015 | Vezina | A01G 9/02 47/66.7 |

OTHER PUBLICATIONS

International Preliminary Report on Patentability in International Application No. PCT/CA2013/050118 dated Aug. 19, 2014.

* cited by examiner

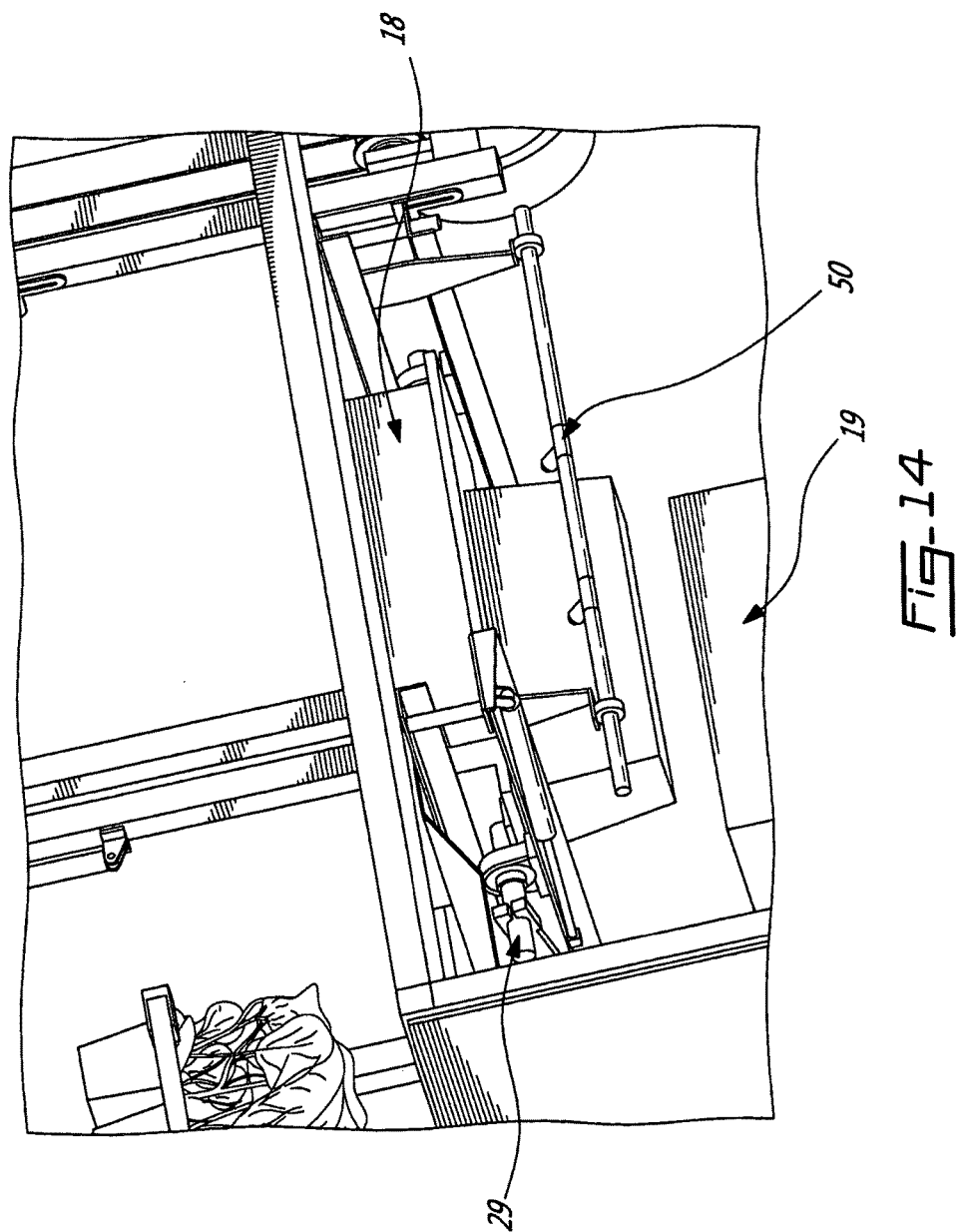

PLANT INFILTRATION DEVICE

CROSS REFERENCE TO RELATED APPLICATION

This application is a national phase application under 35 U.S.C. § 371 of International Application No. PCT/CA2013/050118 filed Feb. 15, 2013, which claims priority from U.S. Provisional Application No. 61/599,094, filed Feb. 15, 2012, the entire content of each of which is incorporated herein by reference.

TECHNICAL FIELD

The present invention relates generally to a device and method for manipulating and infiltrating plants, and more particularly to such a device and method for the automated and high-throughput infiltration of plants used to produce recombinant proteins.

BACKGROUND

There is a resurgence of interest in the production of new therapeutic agents using botanical sources. Genetically engineered plants can now be used to produce pharmacologically active proteins, including mammalian antibodies, blood product substitutes, vaccines, hormones, cytokines, and a variety of other therapeutic agents. Plant production of pharmaceuticals holds great potential, and may become an important production system for a variety of new biopharmaceutical products such as vaccines.

Current influenza vaccines for example are produced in fertilized eggs, which have to be infected and incubated for an extended period of time before the virus can be harvested and purified using an appropriate production system. Vaccine production in insect or mammalian cells also requires an incubation period necessary for the cells to secrete sufficient amounts of virus. When combined with the adaptation that must be made of the target virus (either as an attenuated virus or as subunit viruses) before being introducible into any of those systems, current production methods of candidate vaccines in response to an emerging threat are taking a long time, in addition of having high costs associated with the cells culture or eggs incubation.

Plants are potentially a low cost and contamination safe factory for the production of recombinant pharmaceutical proteins. Most of the recombinant proteins produced in plants are indistinguishable from their mammalian counterparts, as far as the amino acid sequence, conformation and biological activity. Traditionally, proteins have been produced using complex production systems such as cell culture, yeast, bacteria or eggs. However, the ability to produce proteins in plants has several major advantages. Plants are uniquely capable of efficient protein expression of different complexity levels and glycosylation patterns at high yields and low costs Limitations to the application of genetically engineered plants often come from the inability of transgenic organisms to accumulate adequate amounts of the recombinant product, as a result of low transcription rates, improper splicing of the messenger, instability of the foreign mRNA, poor translation rates, hyper-susceptibility of the recombinant protein to the action of endogenous proteases or hyper-susceptibility of the recombinant organism to the foreign protein which result in improper and limited growth or in the worst cases, in strong deleterious effects to the host organism. Inadequacy of production level has a direct impact on the development of applications when profit margins are narrow, or when treatment and/or disposal of residual matter causes bio-safety or environmental problems. Improvement of the accumulation level of the desired recombinant product thus appears to be one critical factor that warrants commercialization of many applications of molecular farming.

Plant-based vaccine manufacturing systems represent a viable alternative to the traditional vaccine development processes, and may provide a more efficient long-term solution to a number of the problems with exist with traditional egg-based or cell-based vaccine production. Plants are cost-effective protein producers, and therefore their use for producing proteins for use in commercial applications, such as but not limited to vaccine development, provides a realistic alternative to more traditional processes used to develop and produce such proteins and/or vaccines. Other uses of such plant-produced proteins include for enzymes for industrial processes, therapeutic antibodies, etc.

The use of Virus-Like Particles (VLPs) is emerging as a technology which has been found well suited for being produced using such plant-based vaccine manufacturing techniques. VLPs generally comprise lipid or protein shells studded with proteins or protein portions, which can be specific to a given disease intended to be targeted by a vaccine. VLPs are thus intended to "look" like a target virus, thereby allowing them to be identified by the immune system of a patient and providing immunity towards that target virus. However because they lack the core genetic material of the actual virus, VLPs are non-infectious and thus cannot replicate. The use of plants for the purposes of producing such VLPs and/or other proteins has been found to be more efficient than certain previously used production processes involving cell cultures, yeast, bacteria, etc., which are typically much more complex and therefore costly.

However, certain challenges nonetheless remain with the use of plants for the commercial production of VLPs and/or proteins, most particularly because previously used systems for the infiltration and processing of plants remain relatively laborious and cost ineffective. Accordingly, improvements in making plant-based vaccine production more commercially viable still remain, in terms of the efficiency and cost effectiveness of production, the quality control and standardization of the produced vaccine, for example.

Therefore, there is a need for an improved device capable of performing the infiltration of plants in automated processes, such as a high-throughput process of candidate proteins for vaccine development and a standardized process for the production of recombinant proteins.

SUMMARY

There has accordingly been developed a high-throughput plant-based recombinant protein production system which permits the acceleration of the discovery and development of new therapeutic compounds such as vaccines antigens by permitting the production of numerous recombinant proteins, including VLPs bearing vaccine candidate antigens for testing. The presently described system permits, for example, the production of a multitude of antigens strategies onto VLPs in plants, which VLPs can then be purified from the plants and tested for the identification of the most efficient VLP-based vaccine against a disease-causing agent. The present system provides a rapid and low-cost production system for the discovery and development of new vaccines using plant-based production techniques.

In accordance with one aspect of the present invention, there is provided a plant infiltration device for infiltrating plants with an inoculum, the device comprising: a frame having one or more tray racks adapted for receiving one or more trays of the plants to be infiltrated, the trays being in an initial position when disposed in the input racks; an automated manipulation mechanism mounted to the frame and operable to displace the plant trays within the device, the manipulation mechanism having a robotic manipulator actuable to at least displace the plant trays from the initial position to an infiltration position; a plurality of inoculum reservoirs mounted to the frame and containing one or more inoculums, the inoculum reservoirs being interconnected in fluid flow communication with a fluid transport system, the fluid transport system being operable to control flow into and out of the inoculum reservoirs; an infiltration tank mounted to the frame and within which the plant trays are received when disposed in the infiltration position, the fluid transport system being in fluid flow communication with the infiltration tank to at least partially fill the infiltration tank with a selected inoculum from one of the inoculum reservoirs to at least partially immerse the plant leaves of the plant tray when disposed in the infiltration position within the infiltration tank, the infiltration tank being enclosed in a sealed configuration when the plant tray is disposed in the infiltration position therein; and a vacuum generating device in communication with the infiltration tank to apply a negative pressure within the infiltration tank in the sealed configuration, thereby opening pores of the plant leaves immersed in the inoculum within the infiltration tank and causing the inoculum to infiltrate into the plant leaves.

In accordance with another aspect of the present invention, there is provided a method of infiltrating a plant with an inoculum using an automated plant infiltration device, the plant being disposed in a tray, the method comprising: providing the plant infiltration device with an infiltration tank within which the plant tray is receivable, at least one inoculum reservoir containing the inoculum and being in independent fluid flow communication with the infiltration tank, and an automated tray manipulation mechanism having a robotic manipulator; feeding the inoculum from the inoculum reservoir into the infiltration tank for infiltrating into the plant; using the robotic manipulator to displace the plant tray from a charging position within the device, wherein the plant tray is fed into the device for infiltration, to an infiltration position, wherein the plant tray is disposed within the infiltration tank such that at least the leaves of the plant are immersed in the selected inoculum fluid within the infiltration tank; enclosing and sealing the infiltration tank with the plant in the infiltration position, and applying a negative pressure within the sealed infiltration tank; and after a predetermined period of time, removing the plant tray from the inoculum fluid within the infiltration tank.

BRIEF DESCRIPTION OF THE DRAWINGS

Reference will now be made to the accompanying drawings.

FIG. 1 is a side perspective view of a plant infiltration device in accordance with one embodiment of the present disclosure, shown with a lower outer panel removed, the plant infiltration device being for infiltrating plants with an inoculum for recombinant proteins production;

FIG. 2 is another perspective view of the plant infiltration device of FIG. 1, shown with the lower outer panel in place;

FIG. 3 is a front perspective view of the plant infiltration device of FIG. 1;

FIG. 4 is an enlarged side elevational view of the plant infiltration device of FIG. 1, showing the inoculum reservoirs;

FIG. 5 is a side elevational view of the opposite side of the plant infiltration device of FIG. 1, shown with outer panels removed;

FIG. 6 is a partial front perspective view of the plant infiltration device of FIG. 1, showing the plant trays in an initial, pre-infiltration, position within tray input racks;

FIG. 7 is an enlarged front elevational view of a plant tray being picked up from the tray input rack by a robotic arm of a manipulation mechanism;

FIG. 8 is an enlarged perspective view of the plant tray being displaced towards above an infiltration tank of the device by the robotic arm of the manipulation mechanism;

FIG. 9 is an enlarged perspective view of the infiltration tank being enclosed and sealed for infiltration of the plants therein with the inoculum solution;

FIG. 10 is an enlarged perspective view of the plant tray, following removal from the infiltration tank, being horizontally displaced by the robotic arm of the manipulation mechanism into a tray output rack;

FIG. 11 is an enlarged perspective view of the robotic arm of the manipulation mechanism following removal of the plant tray from the infiltration tank and displacement into an output rack;

FIG. 12 is a enlarged perspective view of the plant infiltration device of FIG. 1, showing the infiltration tank being emptied;

FIG. 13 is a top perspective view of the infiltration tank of FIG. 11, shown being cleaned; and FIG. 14 is a side perspective view of the infiltration tank of FIG. 12, showing the tank emptying mechanism in more detail.

It will be noted that throughout the appended drawings, like features are identified by like reference numerals.

DETAILED DESCRIPTION

As noted above, plants are potentially a low cost and contamination safe factory for the production of recombinant pharmaceutical proteins. Most of the recombinant proteins produced in plants are indistinguishable from their mammalian counterparts, as far as the amino add sequence, conformation and biological activity. When recombinant proteins are developed using plant-based manufacturing techniques, certain challenges exist which are addressed by the presently described device, including with respect to the manipulation of the plants and the ability to rapidly select and infiltrate one of a number of possible different inoculums into a plant and to be able to rapidly apply a different inoculum, such as to be able to screen for a most desirable inoculum and/or conduct efficient testing following production of such plant-based recombinant proteins.

Accordingly, the plant infiltration device of the present disclosure has been developed in order to be able to rapidly and efficiently process plants to be infiltrated with one of a number of different inoculums, containing the genetic material of interest integrated in a bacteria, such as for example *Agrobacterium*. The presently described plant infiltration device and method is a high-throughput system which enables the rapid expression, purification and testing of recombinant proteins, such as but not limited to vaccines, VLPs based vaccines, recombinant antibodies and/or diagnostic reagent, thereby permitting the production and development of recombinant proteins to be accelerated in comparison with more tradition technologies.

Particularly, VLPs represent an emerging vaccine technology that has numerous advantages over egg-based and cell-based vaccine production technologies. While production of any given vaccine using VLPs produced in plants is faster than production by any other traditional methods, mainly because VLP-based vaccines do not require an actual sample of the virus but only its genetic sequence, the ability to identify and produce the most efficient vaccine against an emerging threat is dependant onto the capability of rapidly and efficiently develop and produce a number of different VLP vaccine candidates against that emerging threat for testing. A particularly limiting step in the development and production of plant-based VLPs is the infiltration step, i.e. the steps of introducing an *Agrobacterium* inoculum containing the genetic information of the targeted viral protein (or any other protein) into the plant. Infiltration being performed into an infiltration tank, the infiltration tank and related tools need to be thoroughly washed and clean from all inoculum before a second, different inoculum is to be used.

As will be seen, the present system enables the rapid screening of the potential of a number of antigens or antigen variants, by being able to easily apply a number of different inoculum formulations to plants in rapid serial sequence. Thus, using the device and method described herein, numerous target proteins can be expressed, thereby permitting a significant library of target proteins to be developed in a relatively short period of time. Of these, the most suitable targets can then be characterized, produced, purified and tested for eventual use in a vaccine.

Figure 2:
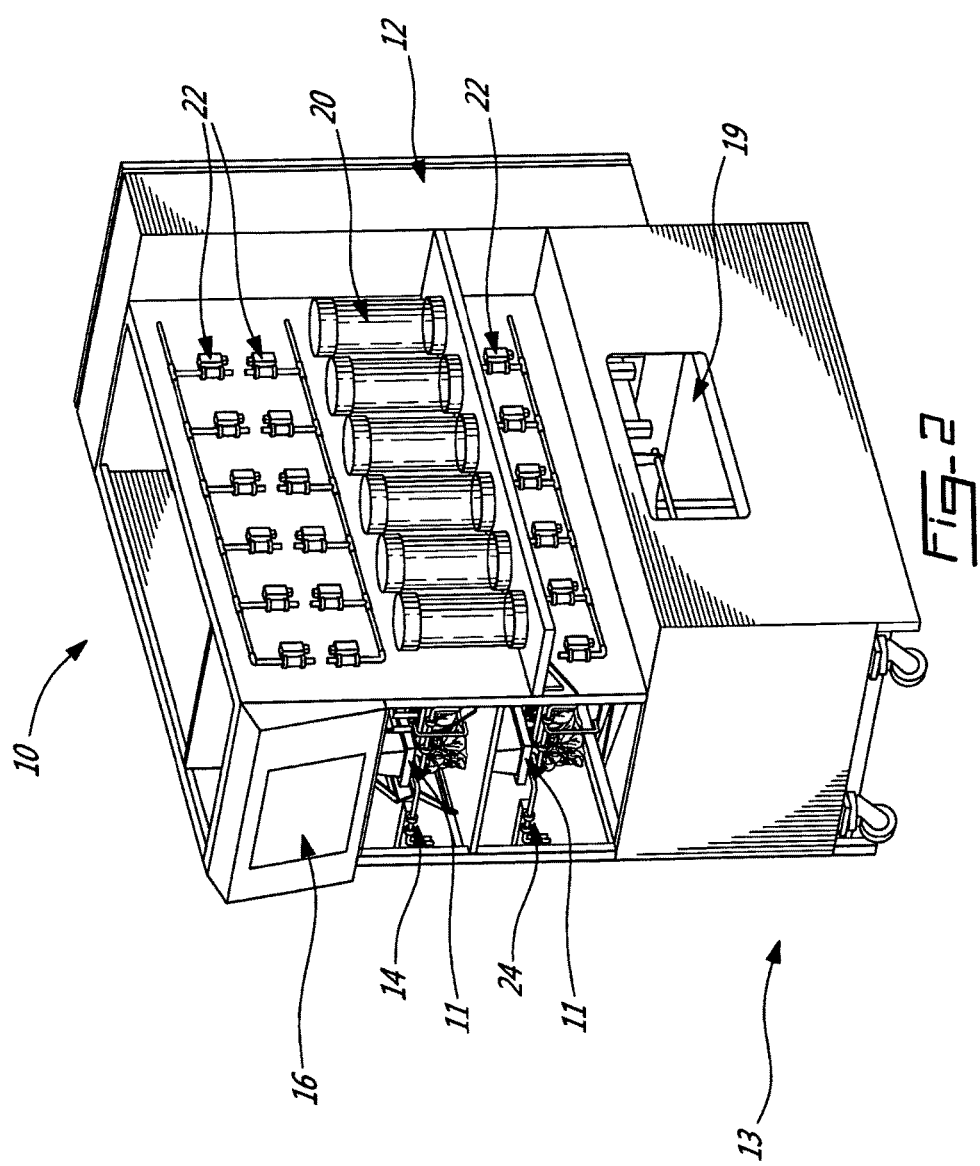
Figure 3:
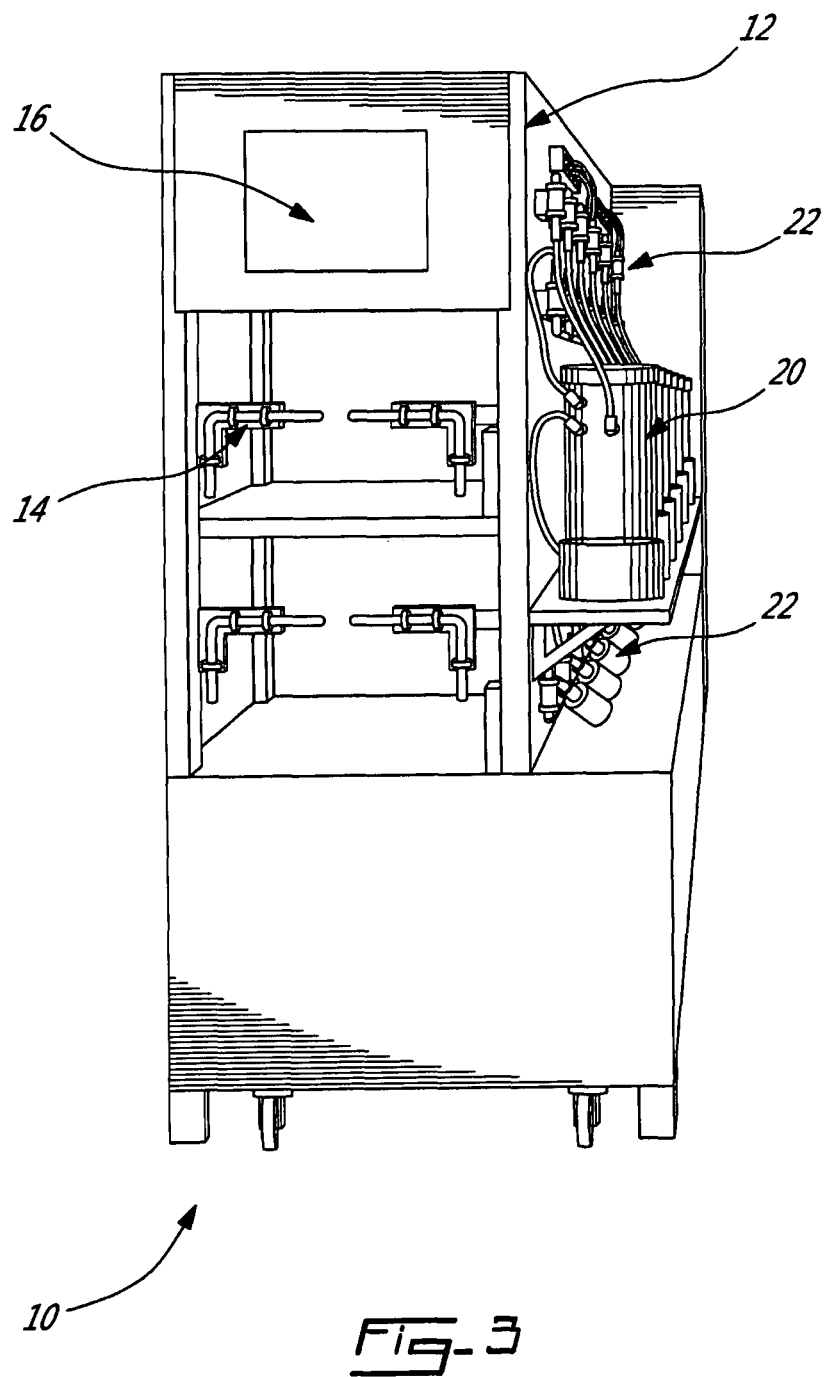

Referring now to FIGS. 1-3, the plant infiltration device 10 of the present disclosure, which is particularly adapted for infiltrating plants with an inoculum for use in recombinant protein production, and particularly in the field of vaccine development, is shown and generally includes a frame 12 or other suitable fixed structure to which the various components are mounted. The device includes, at a front end 13 thereof, a number of plant tray input racks 14, as will be described in further detail below, and a control panel 16. The control panel 16 comprises, in at least one embodiment, a screen which depicts operating conditions of the device and which may be a touch screen enabling control of the operation of the plant infiltration device 10 by the operator. The control panel 16 is therefore connected in electrical communication with a suitable microprocessor or other computer equipment, such as a programmable logic circuit, etc., which make up a control system (not shown), also located within the frame 12 of the device 10, such that a device is independently operable as a stand alone unit. The user may therefore use the control panel in order to activate the device and process plants in the manner described herein, including activating each step individually, programming the device to perform all of the steps by itself, repeating the whole process described herein in loop, selecting a desired inoculum from one of a number provided by the present system, and the rapid changeover from one inoculum to another. Thus, the rapid use of different inoculum solutions on serially sequential plant trays enables a high-throughput screening of the plants infiltrated with a number of candidate inoculums.

As also seen in FIGS. 1-3 and 4, the device includes at least one of inoculum reservoir 20 disposed on a first side of the frame 12 of the device 10, wherein in the case there is a plurality of reservoirs 20 present, each of these independent inoculum reservoirs 20 can be adapted to be able to contain a different inoculum solution such that any one or more of these multiple inoculum solutions may be selected by the operator, either manually or automatically, for infiltration into the plants being processed using the present device 10. Alternatively, some, or even all of the reservoirs 20 can contain the same inoculum where a larger number of plants is infiltrated with the same inoculum is desired. Each of the inoculum reservoirs 20 is connected in fluid-flow communication with an infiltration tank 18, which is itself disposed within the device frame 12, via a fluid transport system 22 which is depicted on a graphically in FIG. 1 but which includes a plurality of fluid conduits and associated valving that is remotely actuable in order to independently control the flow into and out of each or all of the inoculum reservoirs 20. As best seen in FIG. 5, the infiltration tank 18 is disposed part way up within the lower portion of the frame 12, above a larger recuperation tank 19 which is disposed at the base of the lower portion of the frame. As will be described in further detail below, the infiltration tank 18 is rotatably mounted to the frame 12 by pivots axles 29, such that the infiltration tank 18 can be inverted to thereby dump the used inoculum and/or any leaves and plant material that the plants could have lost during the infiltration step, into the recuperation tank 19 therebeneath.

As will be described in further detail below, the infiltration tank 18 can be sized such as to be able to receive at least one of a plant trays 11 and more particularly receive at least one inoculum from an inoculum reservoir 20 at the same time as receiving the plant, with the inoculum being received into the tank 18 before the plant (see FIG. 2) for the purposes of carrying out the infiltration process of the selected inoculum solution. Accordingly, when the plant tray 11 is disposed above or within the infiltration tank 18 in an infiltration position, which correspond to a position of the plant tray 11 by which at least the leaves of the plant are at least partially immersed in the inoculum, the inoculum being previously introduced or added after the plant into the infiltration tank 18 from the selected one of the inoculum reservoirs 20 by the fluid transport system 22, and more particularly by the fluid output piping 25 (see FIG. 4) thereof. The piping system of the upper portions of the fluid transport system 22, located above the inoculum reservoirs 20 in FIG. 1 for example, are generally used to introduce solution, water, etc., into the reservoirs 20.

Figure 6:
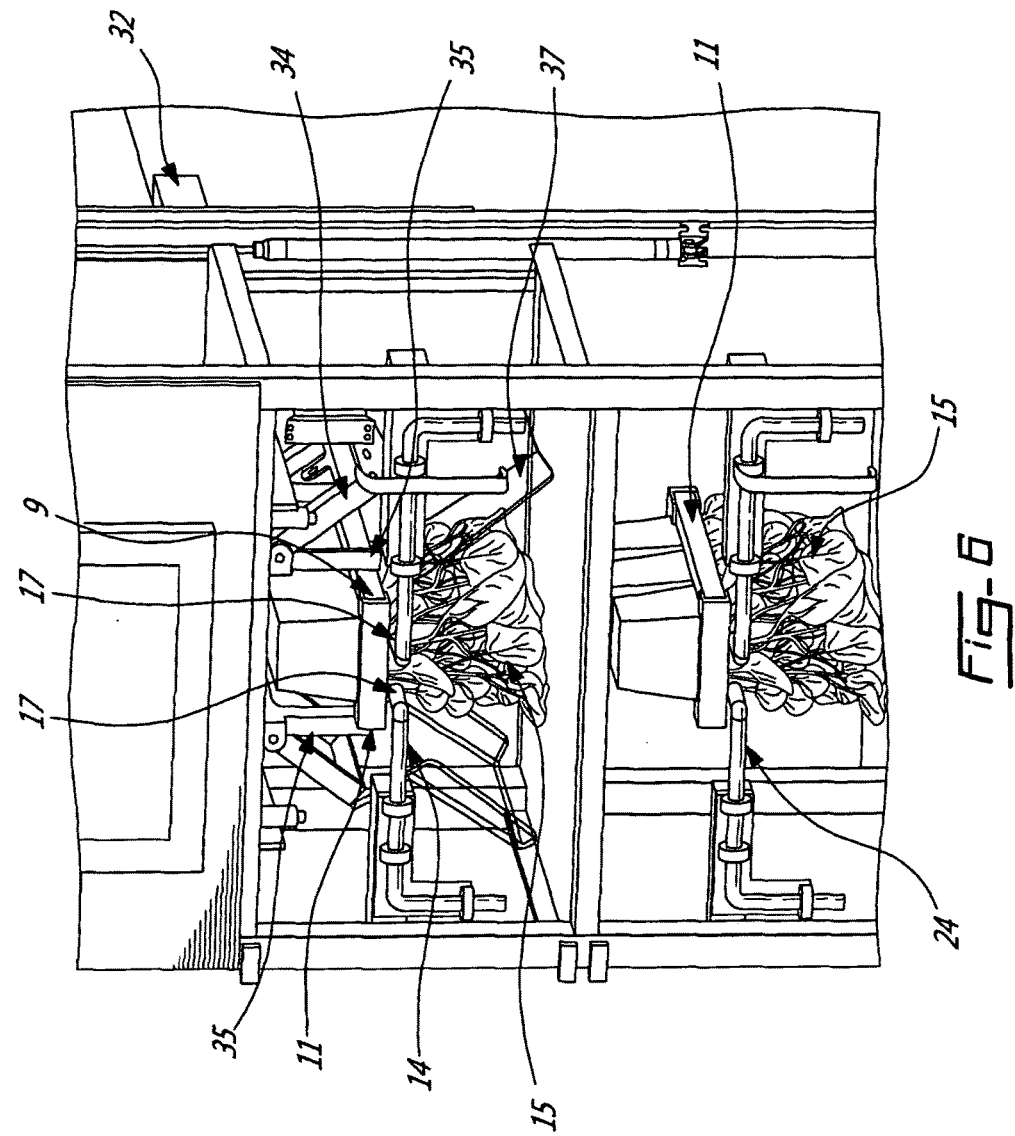
Figure 7:
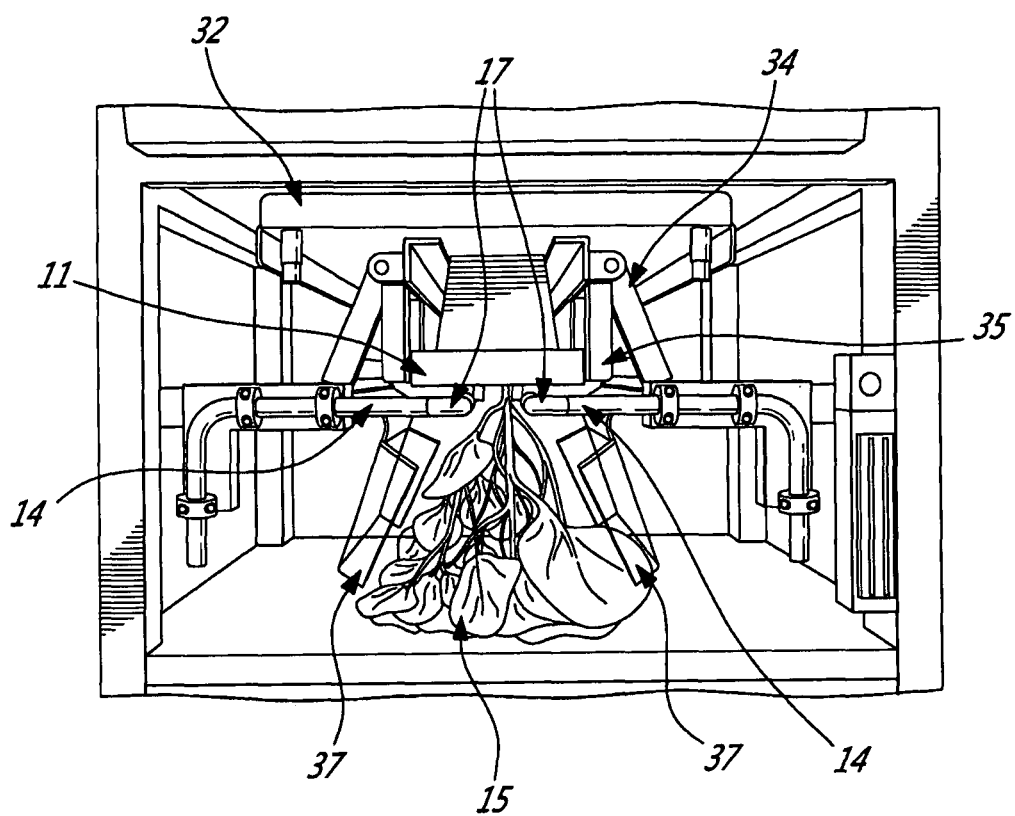

Referring now in more detail to FIGS. 2 and 6-7, the input rack(s) 14 in the front end 13 of the device 10 are more clearly seen. The input rack 14, within which the plants to be processed, may for example comprise at least two supports 17 which are disposed parallel to each other and spaced apart by a distance less than a width of the elongated plant trays 11 in order to support the inverted plant trays 11 and allowing the free sliding of the plants stems. The two parallel supports 17 may be spaced apart from each other a very small distance, such as to form only a relatively narrow gap therebebetween (for example, gaps which are wide enough to fit the plant stems therethrough but which are narrower than the width of the leaves of the plants in the tray 11). This narrow gap enables the plant leaves to be somewhat gathered together when the robotic arm lifts the plant tray vertically off the rack 14, prior to the closing of the covers of the pivoting clamping portions 37, as will be described in further detail below. Although various configurations are possible, in the depicted embodiment of FIGS. 2, 6 and 7, the plant tray 11 is inserted into the input rack 14 upside down, such that the leaves 15 of the plants within the plan tray 11 point downward and are thereby suspended in mid-air by the inverted plan tray 11, which is in turn supported by the supports 17 of the input rack 14. The plant tray 11 can be slid in a longitudinal direction along the rails 17 of the input rack 14, as seen in greater detail in FIGS. 6-7. In the depicted embodiment of the device 10, one input rack 14 is provided, and one output rack 24 is also provided and disposed at a lower elevation within the frame 12 of the device. Accordingly, the plant tray 11 is inserted into the input rack 14 by the operator before being processed by the device 10, and once the process as described herein is carried out for the infiltration of the inoculum into the leaves of the plant, the plant tray 11 is then moved onto the output rack 24 for eventual removal from the device 10 by the operator.

As will be described in further detail below, the present plant infiltration device 10 also includes an automated manipulation mechanism 30 which is mounted to the frame 12 and is operable to displace the plant trays 11 within the device. The manipulation mechanism 30 includes a robotic manipulator 32 (or "robotic arm" 32 as referred to hereinbelow) which is actuable to grasp and release the inverted plant trays 11 without damaging the plants therein. The robotic arm 32 of the manipulation mechanism 30 is therefore operable to displace the plant trays 11 within the device 10, for example in order to move them from the input rack 14 into the infiltration tank 18 for infiltration by the inoculum solution, and to subsequently remove the processed plant tray from the infiltration tank 18 to the output rack 24 or other selected output location within the device.

Figure 4:
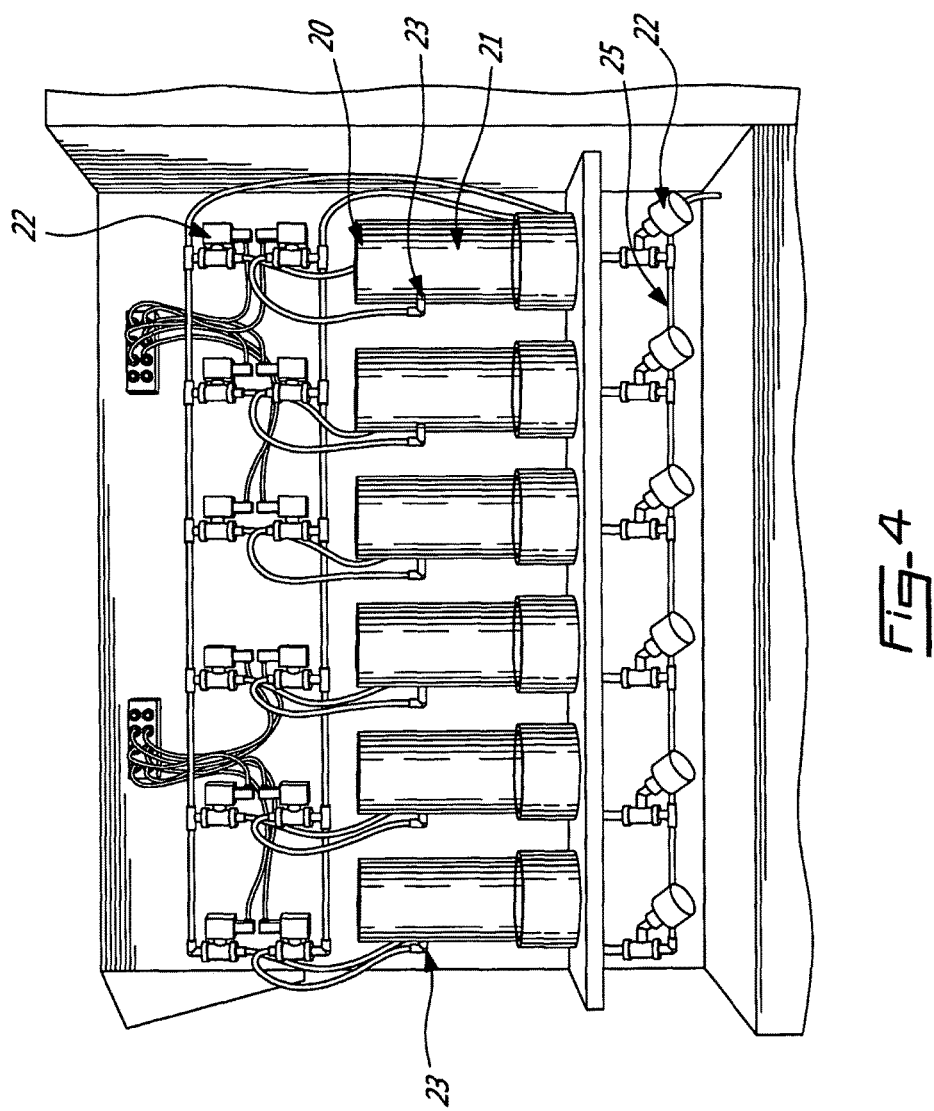
Figure 5:
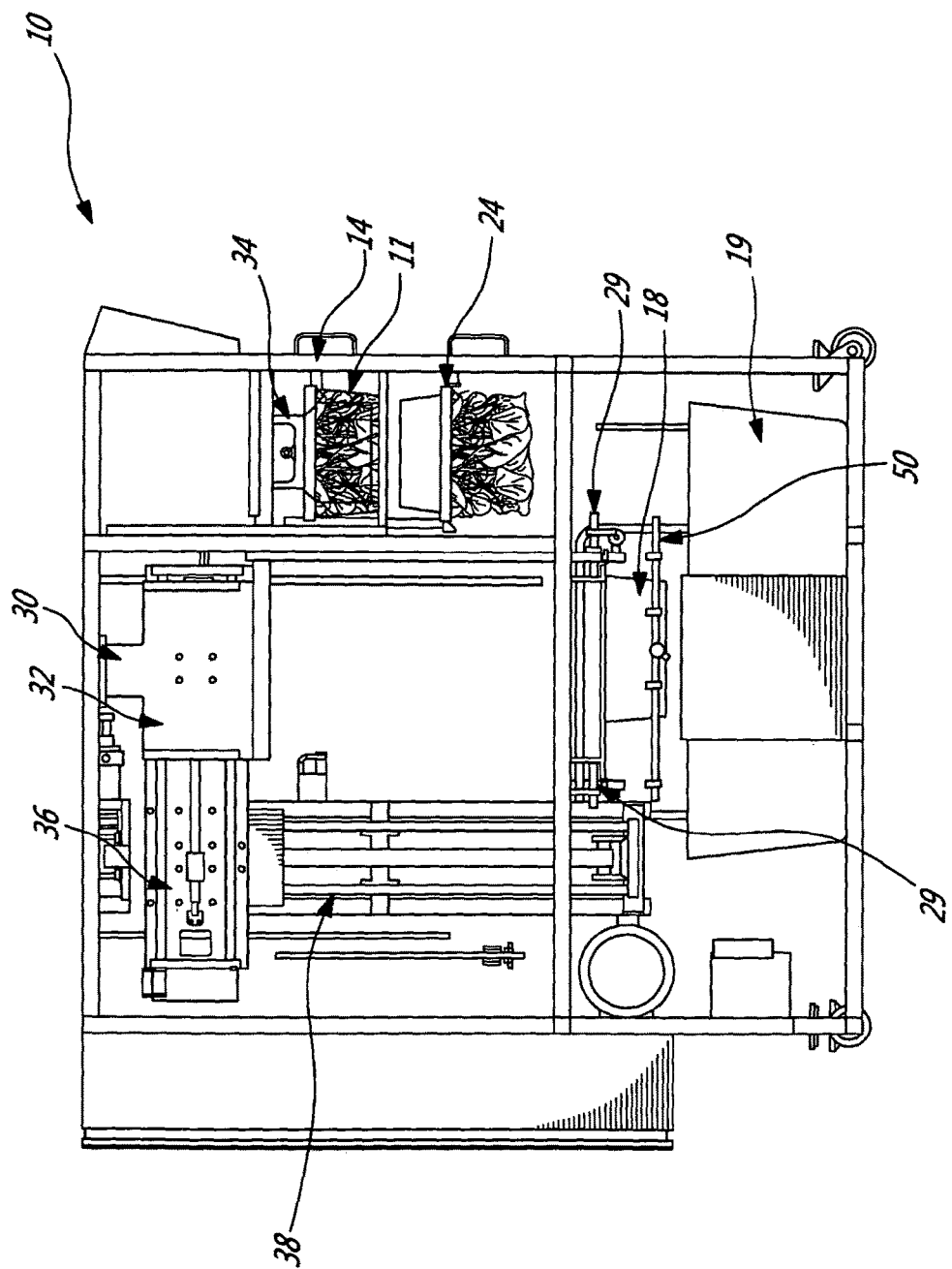

Referring to FIG. 4, the inoculum reservoirs 20 disposed in the side of the frame 12 of the plant infiltration device 10 are seen in greater detail, and may comprise, for example, clear (or at least substantially transparent) tubular cylinders 21 which enable the operator to visually identify, during operation of the device, which of the inoculum reservoirs 20 contains an inoculum solution, how much is contained therein, and to visually acknowledge the washing of the cylinder after use and also which is being used at any given time. Each of these transparent tubular cylinders 21 of the reservoirs 20 has one or more fluid inputs 23 which may be disposed for example in a side wall of the cylindrical reservoir, may comprise a pumping system and which may enable inoculum solution to be fed into each reservoir. Alternatively, the inoculum can be manually added into the reservoir by lifting the top cover of the reservoir, and then adding a suspension solution into the reservoir via the input 23 (which is coming from a suspension solution reservoir within or outside of the device 10). The input or inputs 23 also permit water or other washing fluid to be introduced into the reservoir 20 in order to rinse the reservoir for subsequent use by a different inoculum solution. The fluid transport system 22 therefore includes actuated valves and tubes which interconnect with the input 23 of each reservoir cylinder and which are connected to a fluid source (not shown) in order to provide the input feed of either the inoculum solution or the suspension solution to be introduced or a washing fluid. It is therefore possible to pump or otherwise circulate a washing fluid from its storage reservoir to each of the inoculum reservoirs 20, and then return the washing fluid back to a storage container or to a drain. This washing process can be used to wash each of the reservoirs 20 and all of the associated piping systems and valves. The used washing fluid can also be discharged into the tank 18, thereby also washing the piping between the reservoirs 20 and the infiltration tank 18, whereupon it can then be discharged out of the infiltration tank 18 and into the recuperation tank 19 therebeneath (see FIGS. 1 and 5), in the same manner as the used inoculum solution as described in further detail below. The fluid transport system 22 also includes actuated valves which are interconnected with a fluid output 25 of each of the inoculum reservoirs 20, such that the device 10, via its control system operated by the control panel 16, is able to release the inoculum solution contained in any one of these reservoirs 20 for feeding into the infiltration tank 18. The valves of the fluid transport system 22, which for example control fluid flow to and from the reservoirs 20, may be of any suitable type, for example either manual valves of remotely actuated valves which are operated automatically by the control system by electrical signals and/or alternate fluidic control. While the infiltration tank 18 may be located at a lower elevation than the reservoirs 20, and therefore the feed of the inoculum solution from the selected reservoir 20 into the infiltration tank 18 may be performed by gravity alone, the infiltration tank 18 may also be disposed at the same or at a higher elevation than the reservoirs 20 in which case the fluid output portion 25 of the fluid transport system 22 may be provided with a pumping system operable to introduce the inoculum solution from the selected reservoir 20 into the infiltration tank 18 under pressure.

Referring now to FIGS. 5-7, the manipulation mechanism 30 of the plant infiltration device 10 includes a robotic arm 32 which is displaceable within the confines of the device in order to manipulate and displace the plant trays 11 during the infiltration process. Although other configurations of robotic manipulators are possible, the robotic arm 32 of the manipulation mechanism 30 as depicted includes a plant tray grasping clamp 34 which, as better seen in FIGS. 6 and 7, includes a fixed portion 35 which is configured to slide underneath the outer rim 9 of the plant tray 11 (see FIG. 6) and a pivoting clamping portion 37 which may include covers, which in one particular embodiment are composed of a substantially transparent plastic, that substantially enclose the suspended leaves 15 of the plants within the inverted trays 11 in order to, amongst other things, somewhat compress the leaves into a more compact envelope, thereby permitting a smaller infiltration tank into which they are to be inserted and thus requiring less inoculum solution to be used within the infiltration tank for each infiltration process. Additionally, however, the clamping covers which enclose the plant leaves also help to protect and at least partially enclose the plant leaves 15 during their manipulation within the device, ensuring that all plant leaves will be introduced within the infiltration tank 18 and thus be put in contact with the inoculum solution. Alternately, other configurations of covers of the pivoting clamping portion 37 may be used, however as it is desirable to be able to protect the leaves of the plants during the manipulation thereof, these covers preferably at least partially enclose the plants such as to form a protective enclosure therearound during transport and/or manipulation. Clearly, however, the covers need not be made of plastic and need not be transparent. Regardless, these protective enclosures 37 are actuated to pivot inwardly thereby substantially enclosing the leaves 15 of the plants, following which the tray grasping clamp 34 is actuated by the robotic arm in order to slightly displace the entire tray 11 upwards, thereby disengaging it from contact with the supporting tray racks 14. Alternatively, the protective enclosures 37 can be actuated by other suitable means and/or actuation mechanisms, including downwardly projecting guides which force the closure and opening of the protective enclosures when they abut thereagainst. The plant tray 11 is then longitudinally displaced, inwards towards the center of the device, in a position substantially aligned with the infiltration tank 18, as shown in FIG. 8.

As seen in FIG. 5, the robotic arm 32 therefore enables movement of the plant trays 11 in multiple degrees of freedom within the device, which may include at least two translational degrees of freedom. The robotic arm 32 of the manipulation mechanism 30 may include for example both a horizontal carrier 36 and a vertical carrier 38, which are independently actuated and displaceable relative to each other, such as to enable the robotic arm 32 to displace the plant trays 11 along at least two transversally positioned linear axes. Accordingly, the robotic arm 32 is able to displace the plant trays 11 from their resting position within the input racks 14 into the infiltration position thereof within the infiltration tank 18, and then subsequently from the infiltration tank 18 onto the output rack 24. Other manipulations of the plant trays 11 are also possible, for example rotation about one or more axis of the robotic arm 32 and/or the tray grasping clamp portion 34, for example in order to invert the plant trays 11 either before or after infiltration within the infiltration tank, whereby the robotic arm also enables at least one rotational degree of freedom.

Figure 8:
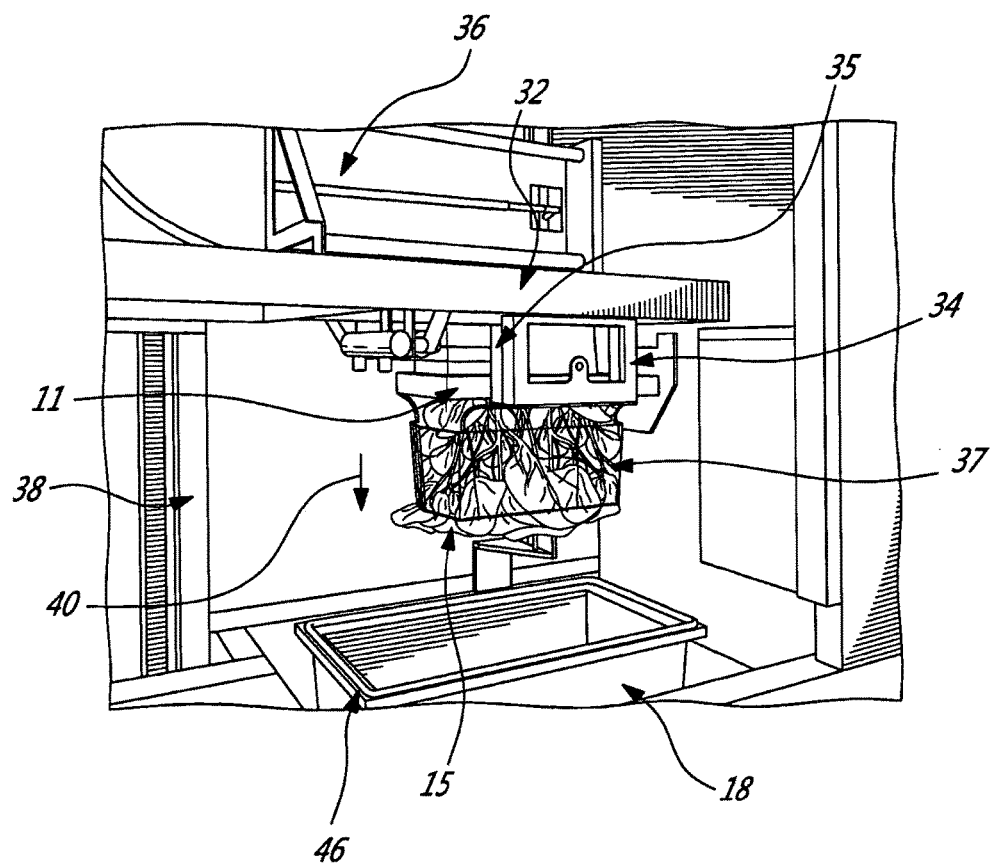

As seen in FIG. 8, an inverted plant tray 11 is shown being displaced by the robotic arm 32 in a substantially vertical direction 40, once sufficient horizontal movement inwardly into the device from the input racks 14 has been carried out such that the plant tray 11 is sufficiently disengaged from the input racks and substantially aligned with the infiltration tank 18 in a vertical direction. Therefore, once the plant tray 11 is vertically aligned with the infiltration tank 18, movement in a horizontal direction is stopped by ceasing actuation of the horizontal carrier 36 of the robotic arm 32, whereupon the aforementioned movement in the vertical direction 40 is initiated by actuating the vertical carrier 38 in order to lower the plant tray 11 down into the open top of the infiltration tank 18. Although alternate tank designs are possible, in the depicted embodiment the infiltration tank 18 comprises generally a tub-like structure having an open top and enclosed sidewalls and bottom, and therefore as such the movement of the plant tray 11 into the infiltration tank 18 occurs by downward vertical displacement. However, the infiltration tank may also be alternately configured, for example having an open side which provides access to the cavity therein, in which case movement of the plant tray 11 would accordingly be substantially horizontal in order to displace the plant tray into the cavity of the infiltration tank 18.

Figure 9:
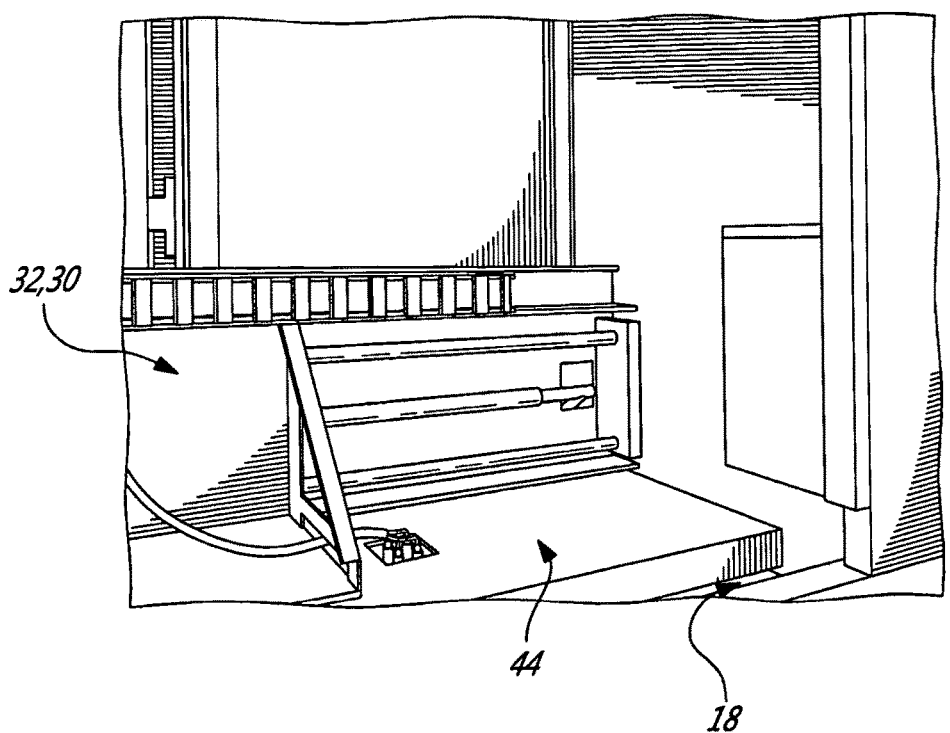
Figure 10:
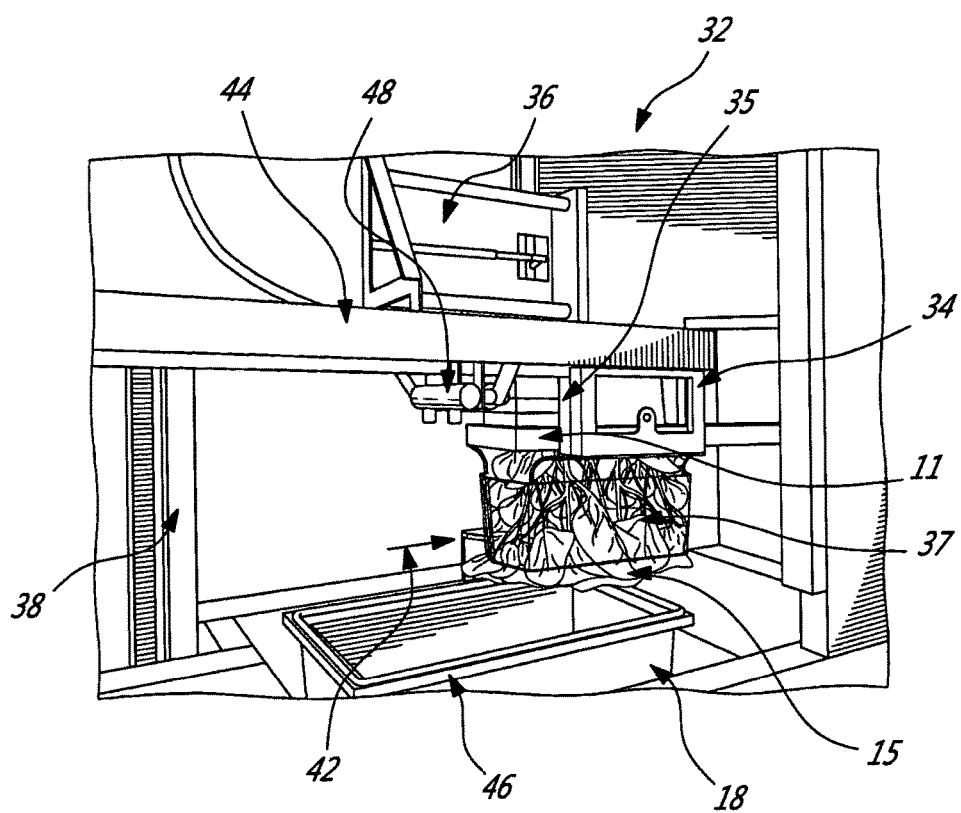

As seen in FIGS. 9-10, once the plant tray 11 has been positioned within the infiltration tank 18 by the robotic arm 32 of the manipulation mechanism 30, the infiltration tank 18 is then enclosed and sealed, with the leaves of the plants to be processed submerged, or at least partially submerged, within the inoculum solution within the infiltration tank 18. Although numerous possibilities exist for an infiltration tank which can be closed and sealed in a manner sufficient to withstand a vacuum pressure as is applied in the present process, as will be discussed below, in the depicted embodiment of the present plant infiltration device 10 this is achieved using a substantially planar tank cover 44 which is mounted to the moveable portion of the robotic arm 32. Accordingly, as the robotic arm 32 manipulates the plant tray 11 into its infiltration position within the infiltration tank 18, the cover 44 is simultaneously brought into sealed abutting engagement with the upper perimeter rim 46 (see FIG. 10) of the open-topped tank 18, thereby fully enclosing the infiltration tank 18 in a sealed manner. Suitable gaskets or other seals may be provided between the perimeter rim 46 and/or the underside of the cover 44 which is brought into contact therewith. Further, the vertical movement of the tank cover 44 in a downward direction, as controlled by the vertical carrier 38 of the robotic arm 32, is selected such that the tank cover 44 is displaced slightly beyond the vertical elevation of the upper rim 46 of the infiltration tank 18 to ensure a tight sealing fit therebetween. Further, additional interlocking or mating alignment members may be provided to ensure a precise alignment between the two sealing surfaces of the tank and the cover, particularly at the very end of the relative vertical movement therebetween. For example, these alignment members may include vertical pins disposed on one of the cover 44 and the tank 18 which mate with corresponding openings in the other component. The alignment members accordingly help to ensure more accurate alignment between the abutting sealing surfaces of the tank and the cover, and also ensure that these abutting sealing surfaces remain perfectly parallel to each other in order to ensure complete sealing therebetween when the tank is placed under a vacuum.

Once the infiltration tank 18 is so enclosed by the cover 44 and sealed closed, a negative pressure is generated within the sealed tank 18 using a vacuum generating device 48 (see FIG. 10) which is in pressure communication with the infiltration tank 18 and the fluid transport system and/or control system of the entire plant infiltration device 10. Although other configurations are possible, in the present embodiment the vacuum generating device 48 is integrated into the portion of the tray grasping clamp 34 of the robotic arm, disposed beneath the cover 44, which accordingly remains enclosed within the infiltration tank 18 when the cover 44 is positioned in its sealed position on the tank. Accordingly, using the vacuum generating device 48, a vacuum is generated within the sealed infiltration tank 18, thereby improving the infiltration of the inoculum solution into the pores of the plant leaves, which are opened due to the vacuum created within the tank.

The plants are maintained in the infiltration tank for a given period of time, which is predetermined in order to best allow the inoculum solution to infiltrate into the pores of the plant. Following this predetermined period of time, the vacuum created within the tank is released, by equalizing pressure within the tank with atmosphere for example, whereupon the plant tray is removed from the inoculum solution and from the tank as described below.

As seen in FIG. 10, once the infiltration of the inoculum solution into the plant has been completed within the infiltration tank 18, the cover 44 is removed from the tank 18 such as to expose and provide access to the plants within tank, and the robotic arm 32 is actuated by the control system of the device 10 to raise the plant tray 11 upwards out of the now-open infiltration tank 18, such that the leaves 15 of the plants are removed from the inoculum solution. In the depicted embodiment of the present device 10, the cover 44 forms part of or is attached to the robotic arm 32, as seen in FIG. 10, and therefore upward movement of the robotic arm 32 simultaneously acts to remove the cover 44 from the tank 18. Alternately, however, the cover need not form part or be connected directly to the robotic arm, in which case the cover would first need to be removed, either by the robotic arm or otherwise, before the robotic arm was able to be actuated to raise by plant tray 11 upwards out of the open infiltration tank 18. The plant tray 11 is then manipulated for removal, for example by horizontally displacing the plant tray 11 in direction 42 outwardly from the center of the device 10 towards an output rack 24 located at the front end 13 of the device. Although the depicted device includes one or more separate output racks 24, which are distinct from the input racks 14 but similarly allow for the plant trays 11 to be suspended therefrom and may for example be located at a lower vertical elevation within the frame of the device, it however remains possible that a single rack may alternately be used for both input and output of the plant trays. However, by providing at least one input rack and at least one output rack, or alternately still several of each, a higher volume and/or higher throughput of plant trays 11 may be processed using the present device 10.

Figure 11:
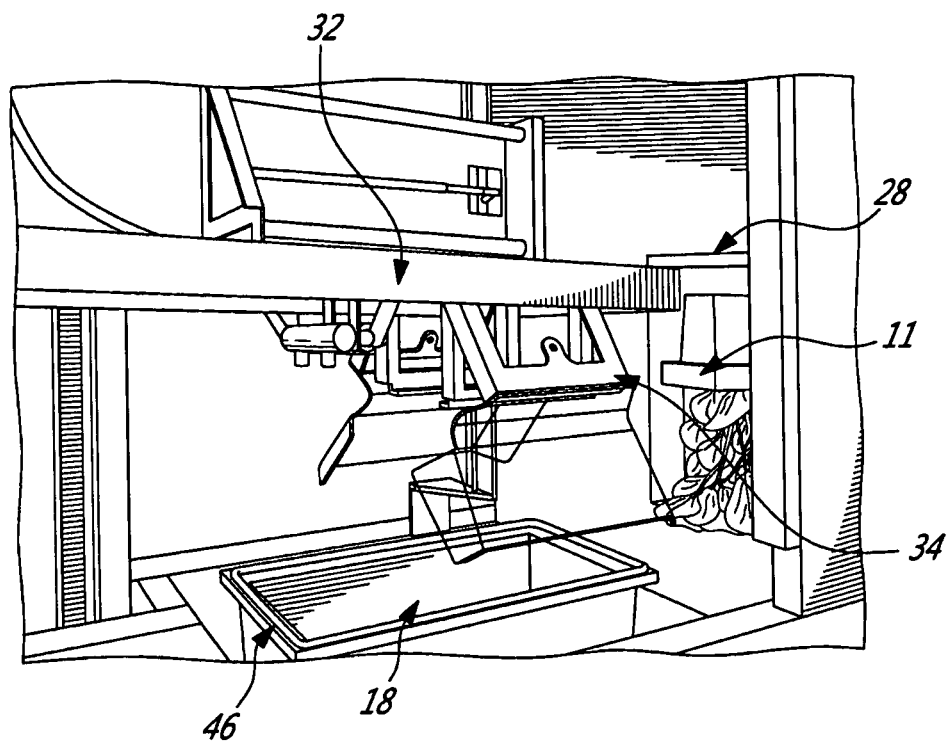

Referring now to FIG. 11, once the plant tray has been set down on the output rack 24, the tray grasping clamp 34 is released, via the outward pivoting of its pivoting clamping portion 37, such as to leave the plant tray 11 suspended on the output rack 24, whereupon the robotic arm 32 displaces the tray grasping clamp 34 back towards the center of the device. In one possible embodiment, sliding doors 28 may be provided in order to separate the input and output racks 14, 24 from the central portion of the device 10 within which the robotic arm operates, for example opening when the device is introducing or removing a plant tray 11 from the infiltration tank 18 and closing during the infiltration and displacement of the plant tray 11. These doors 28 separating the input/output racks and the main infiltration region of the device simply help to prevent any contamination of the plants when suspended in the input and/or output racks and to prevent unwanted displacements of plant trays when positioned in these racks. It also may help having the input racks 11 positioned above the output racks 24, so that no inoculum can contaminate the input racks 11 portions by dripping from the trays 11 being directed towards the output racks 24. Further, simply from a safety standpoint, when closed the doors 28 also act to separate the charging and discharging station (having the input and output racks), which is accessed by the operator of the device, from the robotic arm 30 and other moving parts of the automated manipulation mechanism 30.

Figure 12:
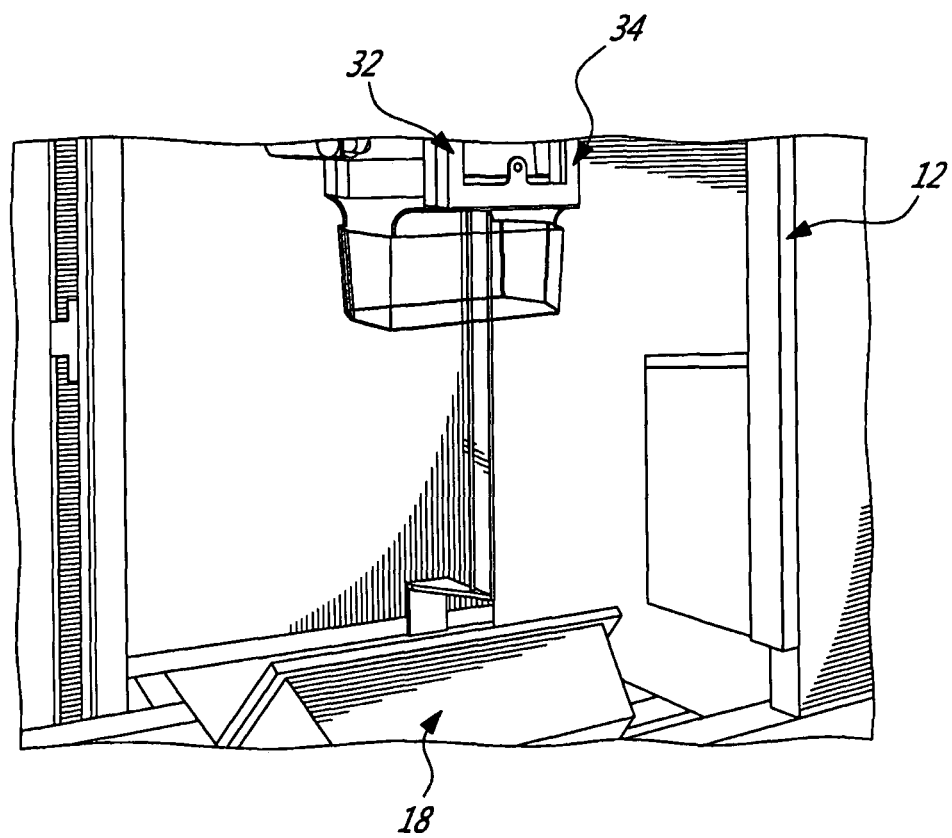

Once the infiltration process for the given plant tray 11 has been completed, the tray grasping clamp 34 of the robotic arm 32 may be moved upwards within the device into its resting position, as shown in FIG. 12, ready for the next plant tray to be processed. The infiltration tank 18, which still contains the inoculum fluid used for the last plant tray processed, can now be emptied, except if it is desirable to use the same inoculum on additional plants. In one possible alternate embodiment, the tank may be emptied using a drain in the base of the tank, which may be operated using gravity or vacuum assistant. However, because it is desirable to also be able to empty any leaves which may have fallen into the infiltration tank 18, in at least the depicted embodiment (see FIGS. 5 and 12-14) the infiltration tank 18 is rotatably mounted within the frame 12 of the device, such that, when actuated, the infiltration tank 18 may be at least partially inverted, for example by rotating it about pivots axles 29 which define a longitudinal axis thereof, in order to allow the inoculum solution and any loose leaves contained therein to be emptied out of the infiltration tank and into a recuperation tank 19 disposed underneath the infiltration tank 18 or to a suitable drain. As noted above, alternate solutions and/or dumping configurations are however also possible, for example by providing a drain directly within the infiltration tank 18, which can be opened and closed as required, thereby permitting the solution within the infiltration tank to be drained when necessary but remaining sealed at other times.

Figure 13:
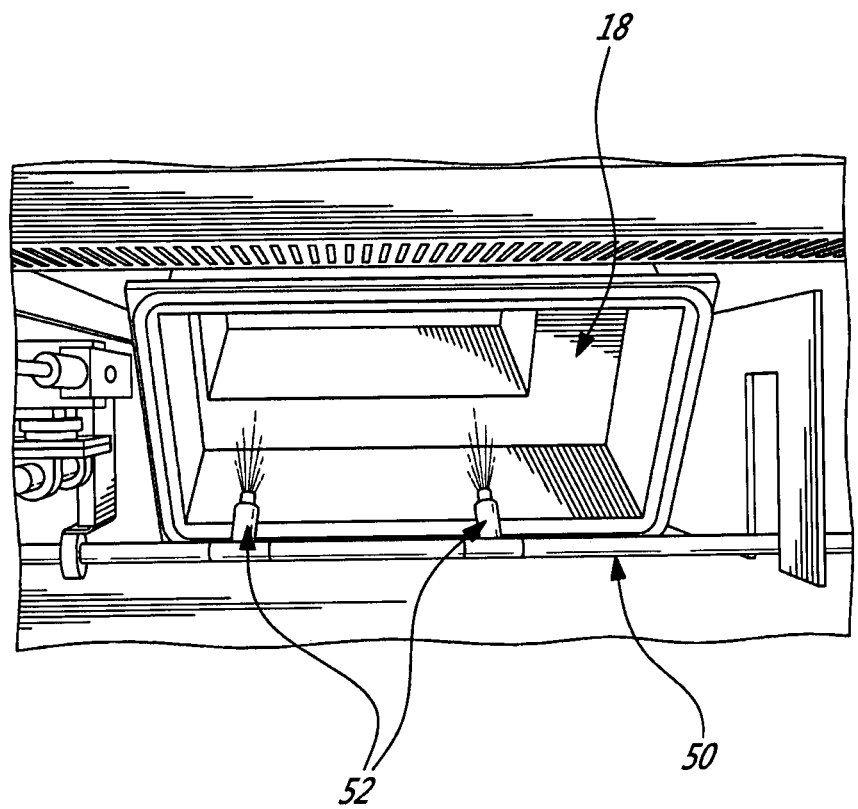

As seen in FIGS. 13 and 14, once the infiltration tank 18 has been so emptied, it is necessary to be able to clean the infiltration tank for further use, and therefore a tank cleaning system 50 is provided which includes several nozzles 52 operable to inject water and/or another rinsing fluid into the infiltration tank 18 in order to permit the interior surfaces of the tank to be rinsed and thereby cleaned. This water or alternate rinsing fluid may then be drained in the manner described above, such as by rotating the tank about its axis in order to invert it and thus dump the cleaning solution or water into the underlying recuperation tank 19.

Each of the steps described above is automated and performed by the plant infiltration device 10 in accordance with a programmable operation to be performed. Because everything can be individually controlled by the operator, using the control system actuated by the control panel 16, the present device 10 can be used to precisely control each infiltration process performed on the plants. For example, a given volume of an inoculum solution can be selected for injection into the infiltration tank from its associated reservoir 20. Similarly, any one of a plurality of different inoculum solutions, each contained in a different one of the reservoirs 20, can be selected by the operator, and further several different inoculum solutions can be used in rapid sequence on different plant trays. All of this permits the rapid and efficient infiltration of numerous possible inoculum solutions with different recombinant proteins, such as candidate vaccines, VLPs based vaccines, recombinant antibodies or diagnostic reagent, into different plants in rapid succession, thereby enabling a high-throughput screening of recombinant proteins inoculums such as for example for an eventual further high-throughput screening of the produced vaccine candidates. The device and methodology described herein allows also the multiple infiltrations of a plant with the same inoculum so as to obtain a greater standardize quantity of a recombinant protein, thereby enabling a high-throughput screening of candidate vaccine inoculums.

The above description is meant to be exemplary only, and one skilled in the art will recognize that changes may be made to the embodiments described without departing from the scope of the invention as defined by the appended claims. Still other modifications which fall within the scope of the present invention, as defined in the appended claims, will be apparent to those skilled in the art, in light of a review of this disclosure.

The invention claimed is:

1. A plant infiltration device for infiltrating plants with an inoculum, the device comprising:
    a frame having one or more tray racks adapted for receiving one or more plant trays of plants to be infiltrated in an infiltration process, the trays being in an initial position when disposed in said racks;
    an automated manipulation mechanism mounted to the frame and operable to displace said plant trays with respect to said racks, the manipulation mechanism having a robotic manipulator actuable to at least displace said plant trays from the initial position to an infiltration position;
    a plurality of inoculum reservoirs mounted to the frame for containing one or more inoculums, the inoculum reservoirs being interconnected in fluid flow communication with a fluid transport system, the fluid transport system being operable to control flow into and out of said inoculum reservoirs;
    an infiltration tank mounted to the frame and retaining a selected inoculum therein, the infiltration tank having a perimeter rim circumscribing a tank opening providing access to an internal cavity of the tank, the plant trays being received within the internal cavity via the tank opening when the plant trays are disposed in said infiltration position, the fluid transport system being in fluid flow communication with said infiltration tank to at least partially fill said internal cavity with the selected inoculum from one of said inoculum reservoirs to at least partially immerse the plant leaves of said plant tray when disposed in said infiltration position within the infiltration tank;

a tank cover mounted in a fixed position to the robotic manipulator, the tank cover abutting the perimeter rim of the infiltration tank when the plant tray is disposed in said infiltration position by the robotic manipulator to form a seal between the tank cover and the infiltration tank, the tank cover remaining engaged to the perimeter rim of the infiltration tank during the infiltration process and being disengaged from the infiltration tank when the robotic manipulator is actuated to displace the plant tray out of said infiltration position following the infiltration process; and a vacuum generating device in communication with said infiltration tank, the vacuum generating device operable to apply a negative pressure within the internal cavity of the infiltration tank with the cover in sealed abutting engagement with the infiltration tank in said infiltration position, thereby opening pores of said plant leaves immersed in said inoculum within the infiltration tank and causing the inoculum to infiltrate into the plant leaves.

2. The plant infiltration device of claim 1, wherein the plurality of inoculum reservoirs are disposed in independent fluid flow communication with the infiltration tank and are independently controlled.

3. The plant infiltration device of claim 1, wherein the inoculum reservoirs comprise a substantially transparent tubular cylinder which visually reveals at least one characteristic of the fluid contents of the inoculum reservoirs.

4. The plant infiltration device of claim 3, wherein the at least one characteristic includes the presence of the inoculum, a total volume of inoculum remaining in each inoculum reservoir and a color of the inoculum.

5. The plant infiltration device of claim 1, further comprising interlocking members respectively disposed on the tank cover and the infiltration tank, the interlocking members matingly engaging each other to ensure precise alignment between sealing surfaces of the infiltration tank and the tank cover.

6. The plant infiltration device of claim 5, wherein said interlocking members include vertical pins disposed on one of the tank cover and the infiltration tank, and mating corresponding openings in the other of the tank cover and infiltration tank.

7. The plant infiltration device of claim 1, wherein the fluid transport system comprises a remotely operable pumping system for pumping the inoculum into and out of said inoculum reservoirs.

8. The plant infiltration device of claim 1, wherein the robotic manipulator comprises a remotely operable robotic arm having at least one plant tray grasping clamp operable to grasp and release said plant trays, and to displace the plant trays in multiple degrees of freedom within the plant infiltration device.

9. The plant infiltration device of claim 8, wherein the plant tray grasping clamp includes a pivoting clamping portion having extending covers which substantially enclose the suspended leaves of the plants within the plant trays.

10. The plant infiltration device of claim 9, wherein the covers of said pivoting clamping portion are composed of a substantially transparent plastic.

11. The plant infiltration device of claim 1, wherein the infiltration tank comprises a drain to empty the infiltration tank, and a recuperation tank beneath the infiltration tank and disposed in fluid communication with said drain.

12. The plant infiltration device of claim 1, wherein the infiltration tank is rotatably mounted by a pivot axle to the frame, the infiltration tank being inverted by rotating said tank about the pivot axle to empty the infiltration tank into a recuperation tank disposed beneath the infiltration tank.

13. The plant infiltration device of claim 1, wherein the infiltration tank comprises a tank cleaning system operable to inject fluid into the infiltration tank.

14. The plant infiltration device of claim 1, further comprising a control system including a control panel mounted to the frame and controlling the automated operation of the plant infiltration device.

15. The plant infiltration device of claim 14, wherein the control panel is connected in electrical communication with a microprocessor programmed to operate the plant infiltration device in accordance with a predetermined operation cycle.

16. The plant infiltration device of claim 1, wherein the inoculum contains a genetic material.

17. The plant infiltration device of claim 16, wherein the genetic material is integrated in a bacterium.

18. The plant infiltration device of claim 17, wherein said bacterium is *Agrobacterium*.

19. A method of infiltrating a plant with an inoculum using a plant infiltration device to perform an automated infiltration process, the plant being disposed in a plant tray, the method comprising:

providing the plant infiltration device with an infiltration tank within which the plant tray is receivable, at least one inoculum reservoir containing said inoculum and being in independent fluid flow communication with the infiltration tank, and an automated tray manipulation mechanism having a robotic manipulator;

feeding the inoculum from the inoculum reservoir into the infiltration tank for infiltrating into the plant;

using the robotic manipulator to displace the plant tray from a charging position within the device, wherein the plant tray is fed into the device for infiltration, to an infiltration position, wherein the plant tray is disposed within the infiltration tank such that at least the leaves of said plant are immersed in the selected inoculum fluid within the infiltration tank;

enclosing and sealing the infiltration tank with the plant in said infiltration position using a tank cover mounted to the robotic manipulator, the tank cover abutting a perimeter rim of the infiltration tank when the plant tray is in the infiltration position, and applying a negative pressure within the infiltration tank sealed by the tank cover, the tank cover remaining engaged to the perimeter rim of the infiltration tank during the automated infiltration process and being disengaged from the infiltration tank when the robotic manipulator is actuated to displace the plant tray out of said infiltration position following the automated infiltration process; and after a predetermined period of time, removing the plant tray from the inoculum fluid within the infiltration tank.

20. The method of claim 19, wherein the automated plant infiltration device includes a plurality of said inoculum reservoirs, the method further comprising feeding the inoculum from a selected one of said inoculum reservoirs into the infiltration tank.

21. The method of claim 20, wherein each of the inoculum reservoirs contains a different inoculum, the method further comprising selecting one of said inoculums from the respective inoculum reservoir for infiltrating into the plants.

22. The method as defined in claim 19, further comprising the step of removing the plant tray from the plant infiltration device to allow for another plant tray to be processed after the step of removing the plant tray from within the infiltration tank.

23. The method as defined in claim 22, further comprising introducing a new plant tray having at least one new plant into the infiltration tank, and repeating at least the steps of feeding the inoculum into the infiltration tank and enclosing, sealing the infiltration tank with the new plant in the infiltration position, and applying a negative pressure within the sealed infiltration tank.

24. The method of claim 19, wherein the inoculum contains a genetic material.

25. The method of claim 24, wherein the genetic material is integrated in a bacterium.

26. The method of claim 25, wherein said bacterium is *Agrobacterium*.

27. The method of claim 19, further comprising the step of inverting the plant tray upside down, the plant disposed therein pointing downwardly in the infiltration position, wherein the plant tray is disposed within the infiltration tank such that at least the leaves of said plant are immersed in the selected inoculum fluid within the infiltration tank.

* * * * *